United States Patent [19]

Martin

[11] 4,073,915
[45] Feb. 14, 1978

[54] TREATING ASTHMA

[75] Inventor: Ulrich Martin, Birsfelden, Switzerland

[73] Assignee: Sandoz Ltd., Basel, Switzerland

[21] Appl. No.: 773,906

[22] Filed: Mar. 3, 1977

Related U.S. Application Data

[63] Continuation-in-part of Ser. No. 686,172, May 13, 1976, abandoned.

[30] Foreign Application Priority Data

May 20, 1975 Switzerland ..................... 6475/75

[51] Int. Cl.$^2$ .......................................... A61K 31/445
[52] U.S. Cl. .................................................. 424/267
[58] Field of Search .......................................... 424/267

[56] References Cited

U.S. PATENT DOCUMENTS 3,272,826  9/1966  Jucker et al. ..................... 260/293.57
3,682,930  8/1972  Bourquin et al. ............... 260/293.57

OTHER PUBLICATIONS

G. P. Gerald et al., Allergologia et Immunopathologia, 4, No. 3, 1976, p. 198.
M. P. Debelic et al., Allergologia et Immunopathologia, 4 (1976), p. 199.
The Pharmocological Bases of Theropeutics, p. 663 (1960).

Primary Examiner—Stanley J. Friedman
Attorney, Agent, or Firm—Gerald D. Sharkin; Robert S. Honor; Thomas O. McGovern

[57] ABSTRACT

The present invention relates to the use of the known compound 4-(1-methyl-4-piperidylidene)-4H-benzo[4,5]cyclohepta[1,2-b]thiophen-10(9H)-one for the prevention and treatment of allergic conditions such as allergic asthma.

11 Claims, No Drawings

TREATING ASTHMA

This is a continuation-in-part of my earlier application Ser. No. 686,172, filed May 13, 1976, now abandoned.

The present invention relates to the known compound 4-(1-methyl-4-piperidylidene)-4H-benzo[4,5]cyclohepta[1,2-b]thiophen-10(9H)-one which is disclosed in our U.S. Patent No. 3,682,930.

It has been found that this compound is useful in the prevention and treatment of allergic conditions, such as allergic gastro-intestinal disorders, exercise-induced asthma, particularly allergic asthma. The compound possesses a histamine release inhibiting activity as indicated in the following standard tests.

The passive cutaneous anaphylaxis (PCA) test in the rat was based on the principles of Mota, J. in Immunology 7, 681 (1964). Female rats (180–200 g) are sensitised by intramuscular administration of 2 mg of egg albumen (Merck No. 967) dissolved in 0.1 ml of physiological saline and 0.5 ml of Haemophilus pertussis vaccine (Schweizerisches Serum and Impfinstitut, Bern; Nr. 115 324; $4 \times 10^{10}$ organism/ml) intraperitoneally. Fourteen days later, the animals are exsanguinated, the blood centrifuged and the serum collected and deep frozen. The serum thus obtained (anti-serum) is injected intradermally (0.1 ml of, for example, a 1:2 diluted serum per injection site) at four sites on the backs of untreated female rats. Twenty-four hours later each rat is administered from about 0.1 mg/kg to about 3.2 mg/kg p.o. or from about 0.056 to about 0.56 mg/kg iv. Either 60 minutes after the oral administration, or immediately or from 5 to 30 minutes afterwards in the case of i.v. administration, egg albumen (5 mg/ml i.v. dissolved in physiological saline containing 0.25% of Evans Blue dye (Merck No. 3169) is administered. The egg albumen elicits a cutaneous anaphylactic reaction, the intensity of which is proportional to the extent to which the Evans Blue dye diffuses into the tissue surrounding each of the four sensitisation sites. Thirty minutes after the administration of the egg albumen, the rats are killed with ether, the underside of the skin of the back of each animal is exposed and the diameter of each area of blue dye surrounding each of the four sensitisation sites is measured. Each dose of the test compound is investigated in between four and six rats and the mean diameter compared with the mean value obtained in four solvent-treated control rats. The percentage inhibition is taken as the percentage of the mean diameter in the controls.

Histamine release inhibiting activity can be confirmed by inhibition of histamine release in the rat peritoneal mast cell test basically as described by Kusner, E. J. et al., J. Pharmacol. Exp. Therap. 184, 41–46 (1973), with the following modification. After sedimentation of the mast cells by centrifugation at $350 \times g$ and 4° C, the sediments are taken up in 1 ml of Hank's balanced salt solution (HBSS) (buffered to a pH of 6.9) and pooled. The resulting suspension is centrifuged, washed again with HBSS and sedimented. The now purified mast cells are prepared as 2 ml suspensions in HBSS. To these are added either 2 ml of HBSS, to determine the spontaneous histamine release, or 2 ml of HBSS and 2.24 mg of compound 48/80 (N-methyl-homoanisylamineformaldehyde condensate; a histamine liberator from Burroughs Wellcome and Co., Inc., Tuckahoe, N.Y., U.S.A.) to determine the 48/80 induced histamine release, or 2 ml of HBSS with 2.24 mg of 48/80 and from 1.80 to 180 mg/ml of the test compound, to determine the 48/80 induced histamine release in the presence of the test compound.

The 48/80 induced histamine release minus the spontaneous histamine release is taken as 100% histamine release. The 48/80 induced histamine release in the presence of the test compound minus the spontaneous histamine release is then compared with the 100% value to determine the percentage inhibition by the test compound. [The histamine determination is effected in conventional manner, for example as described in the above-mentioned Kusner et al. article, or in Kusner and Herzig, Advances in Automated Analysis, 429 (1971)].

For the above-mentioned uses, the dosage to be administered will vary depending on the mode of administration and treatment desired. Satisfactory results are obtained at a daily dosage of from about 0.007 to about 0.14 mg/kg of animal body weight, preferably given in divided doses two to four times daily or in sustained release form. For the larger mammals, the total daily dosage is in the range of from about 0.1 to about 10 mg, suitably from about 0.5 to about 10 mg, especially from about 1 to about 2 mg of the compound, and dosage forms suitable for internal use comprise from about 0.025 to about 5 mg, suitably from about 0.12 to about 5 mg, especially from about 0.25 to about 1 mg in admixture with a solid or liquid pharmaceutically acceptable diluent or carrier.

The compound may be administered in free base or in pharmaceutically acceptable acid addition salt form. Such salts possess the same order of activity as the free base form and are readily prepared in conventional manner. Such salt forms are known and include the hydrogen fumarate.

The invention also provides a pharmaceutical composition comprising the compound or a pharmaceutically acceptable acid addition salt thereof, in association with a pharmaceutically acceptable carrier or diluent.

The compound may be administered orally in the form of tablets, powders, granules, capsules, dragees, suspensions, syrups or elixirs, or parenterally in the form of injectable solutions or suspensions, or as a cream or spray. Oral administration is preferred. Apart from the 4-(1-methyl-4-piperidylidene)-4H-benzo[4,5]-cyclohepta[1,2-b]thiophen-10(9H)-one, the preparations may contain pharmaceutically inert organic or inorganic adjuvants, optionally filling agents, granulating agents, binding agents, lubricants, dispersing agents, wetting agents and preservatives. Moreover, the pharmaceutical preparations may contain colouring, flavouring and sweetening substances, etc. Suitable adjuvants for tablets and capsules are e.g. lactose, microcrystalline cellulose, mannitol, calcium phosphate, starch, alginates, polyvinylpyrrolidone, gelatine, highly dispersed silicic acid, magnesium stearate and talc. Tablet formulations may be coated but are preferably uncoated. Suitable suspending agents for the production of liquid administration forms are especially cellulose derivatives, tragacanth and alginates. Suitable wetting agents are e.g. polyoxyethylene stearate polyoxyethylene polyoxyethylebe sorbitan-monooleate. Furthermore, preservatives such as p-hydroxybenzoic acid alkyl ester may be used.

When the compound is to be administered in the form of a cream, known formulations may be used, e.g. the cream may contain a number of skin compatible additives including a carrier, materials to promote absorption of the substance into the skin, lubricants, wetting agents and lipophilic solvents such as aliphatic alcohols or esters and, if desired, one or more tensides. The aliphatic alcohols and esters should preferably be semi-solid or liquid at room temperature. Suitable tensides include salts of dialkanolamines or trialkanolamines and higher aliphatic carboxylic acids. For use as a spray, the compound may conveniently be dissolved in a suitable solvent, filled into a nebuliser, and administered by conventional inhalation therapy, for example, as an aerosol.

Solid preparations are preferred, especially hard gelatine capsules or tablets, for reasons of easier production and convenience of administration.

The compositions of the invention for internal use suitably contain per unit dosage from about 0.12 to about 5 mg, especially from about 0.25 to about 1 mg of the compound. Where the compositions are already in form ready for administration, the concentration of active ingredient in relation to the composition as a whole may naturally vary within large limits, for example from 0.1% to 95%, e.g. from 0.5 to 90%, in particular from 3 to 50% by weight. Where the compositions require further working up before administration, as for example with liquid concentrates requiring dilution, the concentrations of the active ingredient are suitably such that, after working up in the required manner, for example dilution, the compositions then contain the active ingredient in the concentrations mentioned above.

The compositions of the invention for topical use, for example creams, will naturally contain the active ingredient in a low concentration allowing liberal application of the preparation as required. The concentration of the active ingredient in relation to the whole may, for example, vary from 0.001% to 0.15% by weight.

The following Examples illustrate the invention.

EXAMPLE 1

Capsule

Capsules containing the following constituents can be prepared in known manner and are useful in treating allergic conditions when administered 3 to 4 times a day.

| Constituent | Quantity (mg) |
| --- | --- |
| 4-(1-methyl-4-piperidylidene)-4H-benzo[4,5]cyclohepta[1,2-b]-thiophen-10(9H)-one hydrogen fumarate | 1.375* |
| mannitol | 80.875 |
| corn starch | 56.0 |
| magnesium stearate | 1.4 |
| Aerosil ® 200 (DEGUSSA) (highly dispersed silicic acid) | 0.35 |
| TOTAL | 140.00 |

*equivalent to 1 mg base.

EXAMPLE 2

Tablet

Tablets containing the following constituents can be prepared in known manner and are useful in treating allergic conditions when administered at a dose of one or two tablets 3 times a day.

| Constituent | Quantity (mg) |
| --- | --- |
| 4-(1-methyl-4-piperidylidene)-4H-benzo[4,5]cyclohepta[1,2-b]-thiophen-10(9H)-one | 0.3 |
| polyvinylpyrrolidone | 2.5 |
| lactose | 88.0 |
| corn starch | 4.0 |
| stearic acid | 2.0 |
| talc | 3.2 |
| TOTAL | 100.0 |

EXAMPLE 3

Dragees

Dragees containing the following constituents can be prepared in known manner and are useful in treating allergic conditions when administered at a dose of one or two dragees 3 or 4 times a day.

| Constituent | Quantity (mg) |
| --- | --- |
| 4-(1-methyl-4-piperidylidene)-4H-benzo[4,5]cyclohepta[1,2-b]-thiophen-10(9H)-one | 0.25 |
| polyvinylpyrrolidone | 2.0 |
| lactose | 40.0 |
| stearic acid | 1.0 |
| talc | 2.75 |
| corn starch | 4.0 |
| dragee mass | 50.0 |
| TOTAL | 100.00 |

EXAMPLE 4

Sterile Injectable Solution

The following constituents were dissolved in water and the pH of the solution adjusted to the required value by means of a buffer system. Thereafter, the solution was made up to the requisite final weight by the addition of water. The solution was sealed into 2 ml ampoules and thermally sterilised.

| Constituent | Quantity (mg) |
| --- | --- |
| 4-(1-methyl-4-piperidylidene)-4H-benzo[4,5]cyclohepta[1,2-b]-thiophen-10(9H)-one | 0.5 |
| buffer solution (sodium acetate/conc. acetic acid) | q.s. (for desired pH) |
| sodium chloride | 8.0 |
| water | q.s. (for desired volume) |
| Volume | to 1 ml |

The injectable solution is useful in treating allergic conditions when administered once or twice a day.

EXAMPLE 5

Cream

A foundation was prepared from wool-wax and liquid paraffin, sterilised, and a sterile solution of 4-(1-methyl-4-piperidylidene)-4H-benzo[4,5cyclohepta[1,2-b]thiophen-10(9H)-one emulsified in the foundation.

| Constituent | Quantity (wt/vol) | |
| --- | --- | --- |
| 4-(1-methyl-4-piperidylidene)-4H-benzo[4,5]cyclohepta[1,2-b]-thiophen-10(9H)-one hydrogen fumarate | 0.050 | g |
| wool-wax | 525.0 | g |
| liquid paraffin | 130.0 | g |
| distilled water | 180.0 | ml |

The cream is useful in treating allergic conditions when administered as required.

EXAMPLE 6

Tablets containing the following constituents can be prepared in known manner and are useful in treating allergic conditions when administered at a dose of one or two tablets three times a day.

| Constituent | Quantity (mg) |
| --- | --- |
| 4-(1-methyl-4-piperidylidene)-4H-benzo[4,5]cyclohepta[1,2-b]-thiophen-10(9H)-one hydrogen fumarate | 1.375* |
| Corn starch (partly dried) | 9.5 |
| Anhydrous calcium hydrogen phosphate 87% by weight Corn starch 13% by weight | 177.225 |
| Magnesium stearate | 1.9 |
| TOTAL: | 190.0 |

*~1 mg of free base form

Aerosols containing the constituents referred to in Examples 7 to 9 can be prepared in known manner and are useful in treating allergic conditions when administered as required. The aerosols may suitably be contained in 9 ml aerosol phials.

EXAMPLE 7

| Constituent | Quantity (mg) |
| --- | --- |
| 4-(1-methyl-4-piperidylidene)-4H-benzo[4,5]cyclohepta[1,2-b]-thiophen-10(9H)-one hydrogen fumarate | 138.0* |
| Lecithin | 5.0 |
| Ethanol (absolute) | 240.0 |
| Frigen 113 TR ($C_2Cl_3F_3$) | 1000.0 |
| Frigen 11/12/114 (25:50:25) ($CCl_3F$, $CCl_2F_2$, $C_2Cl_2F_4$) | 2000.0 |
| TOTAL: | 3383.0 |

*~100 mg of free base form

EXAMPLE 8

| Constituent | Quantity (mg) |
| --- | --- |
| 4-(1-methyl-4-piperidylidene)-4H-benzo[4,5]cyclohepta[1,2-b]-thiophen-10(9H)-one hydrogen fumarate | 138.0* |
| Dipalmityl lecithin | 5.0 |
| Ethanol (absolute) | 240.0 |

| Constituent | Quantity (mg) |
| --- | --- |
| Frigen 113 TR ($C_2Cl_3F_3$) | 1000.0 |
| Frigen 11/12/114 (25:50:25) ($CCl_3F$, $CCl_2F_2$, $C_2Cl_2F_4$) | 2000.0 |
| TOTAL: | 3383.0 |

*~100 mg of free base form

EXAMPLE 9

| Constituent | Quantity (mg) |
| --- | --- |
| 4-(1-methyl-4-piperidylidene)-4H-benzo[4,5]cyclohepta[1,2-b]-thiophen-10(9H)-one hydrogen fumarate | 138.0* |
| Ethanol (absolute) | 240.0 |
| Frigen 113 TR ($C_2Cl_3F_3$) | 1000.0 |
| Frigen 11/12/114 (25:50:25) | 2000.0 |

| Constituent | Quantity (mg) |
| --- | --- |
| ($CCl_3F$, $CCl_2F_2$, $C_2Cl_2F_4$) | |
| TOTAL: | 3378.0 |

*~100 mg of free base form

Syrups containing the constituents referred to in Examples 10 and 11 can be prepared in known manner and are useful for treating allergic conditions when administered as prescribed. The syrups are particularly suitable for treating allergic conditions in children.

EXAMPLE 10

| Constituent | Quantity (kg) |
| --- | --- |
| 4-(1-methyl-4-piperidylidene)-4H-benzo[4,5]cyclohepta[1,2-b]-thiophen-10(9H)one hydrogen fumarate | 0.138* |
| Flavouring | 0.06105 |
| Nipakombin B (67% p-oxybenzoyl methyl ester 33% p-oxybenzoyl proply ester) | 0.250 |
| Anhydrous citric acid (powder) | 1.050 |
| Anhydrous disodium hydrogen phosphate | 1.600 |
| Ethanol(94% G/G) | 10.000 |
| Sucrose (crystals) | 150.000 |
| Sorbitol (70% G/G) | 250.000 |
| Demineralised water to | 612.500 |

*~0.1 kg of free base form

EXAMPLE 11

| Constituent | Quantity (g) |
| --- | --- |
| 4-(1-methyl-4-piperidylidene)-4H-benzo[4,5]cyclohepta[1,2-b]-thiophen-10(9H)-one hydrogen fumarate | 5.52* |
| Flavouring | 2.44 |
| Nipakombin B (67% p-oxybenzoyl methyl ester 33% p-oxybenzoyl propyl ester) | 10.0 |
| Anhydrous citric acid (powder) | 42.0 |

| Constituent | Quantity (g) |
| --- | --- |
| Anhydrous disodium hydrogen phosphate | 64.0 |
| Ethanol (94% G/G) | 400.0 |
| Polysorb 80/85 (hydrogenated glucose syrup) | 16,000.0 |
| Demineralised water to give final volume of | 20.0 l |

*~4.00 g of free base form

What is claimed is:

1. A method of preventing or treating allergic asthma, exercise-induced asthma and allergic gastrointestinal disorders which comprises administering to an animal in need of such treatment an effective amount of the compound 4-(1-methyl-4-piperidylidene)-4H-benzo[5,4]cyclohepta[1,2-b]thiophen-10(9H)-one.

2. The method of claim 1, wherein the compound is internally administered at a daily dosage of from about 0.007 to about 0.14 mg/kg of animal body weight.

3. The method of claim 1, wherein the compound is internally administered at a daily dosage of from about 0.1 to about 10 mg.

4. The method of claim 1, wherein the compound is internally administered at a daily dosage of from about 0.5 to about 10 mg.

5. The method of claim 1, wherein the compound is internally administered at a daily dosage of from about 1 to about 2 mg.

6. The method of claim 1, wherein the compound is internally administered in unit dosage form containing from about 0.025 to about 5 mg of the compound.

7. The method of claim 1, wherein the compound is internally administered in unit dosage form containing from about 0.12 to about 5 mg of the compound.

8. The method of claim 1, wherein the compound is internally administered in unit dosage from containing from about 0.25 to about 1 mg of the compound.

9. The method of claim 1, wherein the compound is administered topically.

10. The method of claim 1, wherein the compound is administered in the form of a pharmaceutically acceptable acid addition salt.

11. The method of claim 10, wherein the compound is administered in the form of the hydrogen fumarate.

* * * * *